United States Patent
Angott et al.

(10) Patent No.: US 10,045,698 B2
(45) Date of Patent: *Aug. 14, 2018

(54) APPARATUS AND METHOD FOR DETECTING A PRESENCE OF CANCER

(71) Applicant: First Sense Medical, LLC, Pontiac, MI (US)

(72) Inventors: Paul G. Angott, Bloomfield Hills, MI (US); Pavan Vempaty, Auburn Hills, MI (US); Steven Henke, Canton, MI (US); Ajay Mudunuri, Detroit, MI (US)

(73) Assignee: First Sense Medical, LLC, Mesa, AZ (US)

( * ) Notice: Subject to any disclaimer, the term of this patent is extended or adjusted under 35 U.S.C. 154(b) by 747 days.

This patent is subject to a terminal disclaimer.

(21) Appl. No.: 14/657,357

(22) Filed: Mar. 13, 2015

(65) Prior Publication Data

US 2015/0257650 A1 Sep. 17, 2015

Related U.S. Application Data (60) Provisional application No. 61/952,332, filed on Mar. 13, 2014.

(51) Int. Cl.
*A61B 5/00* (2006.01)
*A61B 5/01* (2006.01)
*A61B 10/00* (2006.01)

(52) U.S. Cl.
CPC ............ *A61B 5/0091* (2013.01); *A61B 5/004* (2013.01); *A61B 5/0013* (2013.01); *A61B 5/015* (2013.01);
(Continued)

(58) Field of Classification Search
CPC ....... A61B 5/0091; A61B 5/418; A61B 5/015; A61B 5/004; A61B 5/0013; A61B 5/4312;
(Continued)

(56) References Cited

U.S. PATENT DOCUMENTS 4,015,537 A * 4/1977 Graef ..................... B61B 13/00
104/107
4,428,382 A 1/1984 Walsall et al.
(Continued)

FOREIGN PATENT DOCUMENTS

CN 102908124 A 2/2013
WO 9529652 A1 11/1995
(Continued)

OTHER PUBLICATIONS

International Search Report dated Jun. 24, 2015.
Written Opinion dated Jun. 24, 2015.

*Primary Examiner* — Bo J Peng
(74) *Attorney, Agent, or Firm* — Dickinson Wright PLLC (57) ABSTRACT

A diagnostic apparatus (20) for detecting a presence of breast cancer in a patient disposed in a testing position. The diagnostic apparatus (20) includes a housing (44) and a camera assembly (58) that is supported by the housing (44) for recording images of the breasts of the patient. A rail (76) is supported by and extends from the housing (44) and terminates at a pair of rail ends (80). A trolley (88) interconnects the camera assembly (58) and the rail (76) and is slideable along said rail (76) for providing movement of the camera assembly (58) along the rail (76) between the rail ends (80) for allowing the camera assembly (58) to consecutively record images at different positions along the rail (76) and to record images of the lymph nodes of the patient when the camera assembly (58) is disposed adjacent to the
(Continued)

rail ends (80) in alignment with the sides of the breasts of the patient.

19 Claims, 9 Drawing Sheets

(52) U.S. Cl.
CPC ............ *A61B 5/418* (2013.01); *A61B 5/4312* (2013.01); *A61B 10/0041* (2013.01); *A61B 2560/0233* (2013.01); *A61B 2560/0437* (2013.01); *A61B 2562/0271* (2013.01)

(58) Field of Classification Search
CPC ........ A61B 10/0041; A61B 2560/0437; A61B 2560/0233; A61B 2562/0271
See application file for complete search history.

(56) References Cited

U.S. PATENT DOCUMENTS

| | | | |
|---|---|---|---|
| 4,548,212 A | 10/1985 | Leung | |
| 4,648,697 A * | 3/1987 | Kawazoe | F16M 11/105 |
| | | | 248/163.1 |
| 4,699,484 A * | 10/1987 | Howell | F16M 11/10 |
| | | | 352/132 |
| 4,844,768 A * | 7/1989 | Kimura | B29D 30/3007 |
| | | | 156/361 |
| 5,603,328 A * | 2/1997 | Zucker | A61B 5/015 |
| | | | 250/330 |
| 5,810,010 A | 9/1998 | Anbar | |
| 6,077,228 A | 6/2000 | Schonberger | |
| 6,336,625 B1 * | 1/2002 | Liao | B25B 27/304 |
| | | | 254/10.5 |
| D480,406 S * | 10/2003 | Tudico | D16/215 |
| 7,037,006 B2 * | 5/2006 | Chapman | B66F 11/048 |
| | | | 212/195 |
| 7,154,397 B2 | 12/2006 | Zerhusen et al. | |
| 7,292,719 B2 | 11/2007 | Arnon | |
| 7,558,618 B1 | 7/2009 | Williams | |
| 8,256,899 B1 * | 9/2012 | Shields | G03B 15/00 |
| | | | 348/208.2 |
| 8,620,041 B2 | 12/2013 | Arnon et al. | |
| 8,670,037 B2 | 3/2014 | Arnon et al. | |
| 8,913,803 B2 | 12/2014 | Arnon | |
| 8,914,925 B2 | 12/2014 | Angott | |
| 2005/0081737 A1 * | 4/2005 | Smallwood | B60J 5/14 |
| | | | 104/89 |
| 2005/0103353 A1 | 5/2005 | Grahn et al. | |
| 2005/0135800 A1 * | 6/2005 | Nguyen | G03B 7/10 |
| | | | 396/463 |
| 2007/0058845 A1 | 3/2007 | Diakides et al. | |
| 2008/0077005 A1 | 3/2008 | Piron et al. | |
| 2008/0260255 A1 | 10/2008 | Szu | |
| 2010/0312136 A1 | 12/2010 | Cozzie | |
| 2010/0324379 A1 | 12/2010 | Clark et al. | |
| 2011/0021944 A1 | 1/2011 | Arnon et al. | |
| 2011/0243409 A1 | 10/2011 | Naimi et al. | |
| 2012/0050321 A1 | 3/2012 | Arieli et al. | |
| 2012/0274775 A1 * | 11/2012 | Reiffel | G06Q 30/0241 |
| | | | 348/158 |
| 2013/0030304 A1 | 1/2013 | Chung-Ming | |
| 2013/0116573 A1 | 5/2013 | Herman | |
| 2014/0098236 A1 * | 4/2014 | Holliday | G01J 5/026 |
| | | | 348/164 |

FOREIGN PATENT DOCUMENTS

| | | |
|---|---|---|
| WO | 0156527 A1 | 8/2001 |
| WO | 2009118721 A1 | 10/2009 |

\* cited by examiner

APPARATUS AND METHOD FOR DETECTING A PRESENCE OF CANCER

CROSS REFERENCE TO RELATED APPLICATION

This application claims the benefit of U.S. provisional patent application Ser. No. 61/952,332 filed Mar. 13, 2014, and entitled "ADVANCED THERMOGRAPHIC IMAGING DIAGNOSTIC APPARATUS AND METHOD", the entire disclosure of which is hereby incorporated by reference.

BACKGROUND OF THE INVENTION

1. Field of the Invention

A diagnostic apparatus for detecting a presence of breast cancer in a patient.

2. Description of the Prior Art

Various diagnostic apparatuses and methods are utilized in the fields of cancer research and treatment to detect a presence of cancer in patients. Known apparatuses often utilize at least one stationary thermographic camera for recording thermographic images of the breasts of the patient which are thereafter analyzed to detect symptoms of cancer. Such diagnostic apparatuses typically require ether a plurality of stationary thermographic cameras or a shifting of the entire diagnostic apparatus relative to the patient to record thermographic images of the breasts. One such diagnostic apparatus is disclosed in U.S. Pat. No. 7,292,719 to Boaz Arnon. Even with multiple thermographic cameras or relative movement of the diagnostic apparatus, the resultant thermographic images often do not adequately capture all aspects of the breasts necessary to conduct a complete analysis of the breasts to detect for the presence of breast cancer. Accordingly, these systems and methods do not complete a thorough analysis of the breasts of the patient and thus may lead to the test results in some cases being inaccurate. Additionally, these apparatuses suffer from other drawbacks, such as high equipment and operation costs for doctors that are ultimately passed onto patient, necessarily reducing the number of patients who participate in the breast screening due to its high out-of-pocket expense.

Other known diagnostic apparatuses and methods of detecting a presence of cancer subject the patient to a cold stress for a predetermined period of time during the diagnostic test. The use of the cold stress is based on the recognition that blood vessels that feed cancerous tumors in breasts, i.e., angiogenic blood vessels, have a different anatomical structure than normal blood vessels, causing such angiogenic blood vessels to constrict to a lesser degree than normal blood vessels in response to a cold stimulus that is applied to the body of a patient. As such, the temperature associated with normal blood vessels decreases to a greater extent than angiogenic blood vessels when the body of the patient is exposed to the cold stimulus.

One example of a diagnostic apparatus and method utilizing a cold stress is disclosed in U.S. Pat. No. 7,558,618 to Darin S. Williams (hereinafter "Williams"). As set forth in the background section of Williams, a control thermographic image of the breasts of the patient is first recorded, after which the hands of the patient are subjected to a cold stress by placing the hands of the patient in a bucket of ice water. After the hands of the patient are cold stressed, a test thermographic image of the breasts of the patient is recorded. The control and test thermographic images are compared with one another to identify regions of the breasts in which the temperature remained substantially unchanged after the cooling of the hands.

Like the previously mentioned diagnostic apparatuses and methods, these cold stress apparatuses and methods do not adequately capture all aspect of the breasts necessary for an accurate detection of breasts cancer at least in part because stationary cameras are utilized. Furthermore, such apparatuses and methods require a technician to be in the room at all times to facilitate the application of the cold stress and to record the thermographic images of the patient. Therefore operational costs necessarily increase from the added labor costs, leading to higher out-of-pocket expense for patients. Additionally the patient is afforded low levels of privacy when they disrobe for the recording of thermographic images. These factors are known to make patients weary of undergoing such examinations, and reduce the number of patients who participate in breast screening.

Accordingly, there remains a need for apparatuses and methods of detecting cancer that are more accurate, reliable, affordable and provide for high levels of privacy for a large number of patients.

SUMMARY OF THE INVENTION

A diagnostic apparatus for detecting a presence of breast cancer in a patient includes a rail extending from a housing. A trolley supports the camera assembly and is slideably disposed along the rail for allowing the camera assembly to consecutively record images of breasts of the patient at different positions along the rail.

Advantages of the Invention

The invention in its broadest aspect therefore provides for an imaging apparatus that easily and reliably records images of the breasts of a patient at various positions, including positions that capture lymph nodes on the sides of the breasts of the patient. Additionally, the apparatus is simple in design and inexpensive to operate, which ultimately can save money for both doctors and patients. More specifically, since the overall system is simpler and less expensive than the prior art systems, this leads to the breast cancer test being accessible to more patients. In other words, lower upfront tester and operation costs ultimately provides for lower examination costs for patients, thus reducing or eliminating the cost barriers for patient participation. As a result, the subject diagnostic apparatus is accessible to more patients which leads to increased participation in breast cancer screenings.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENTS

Figure 5:
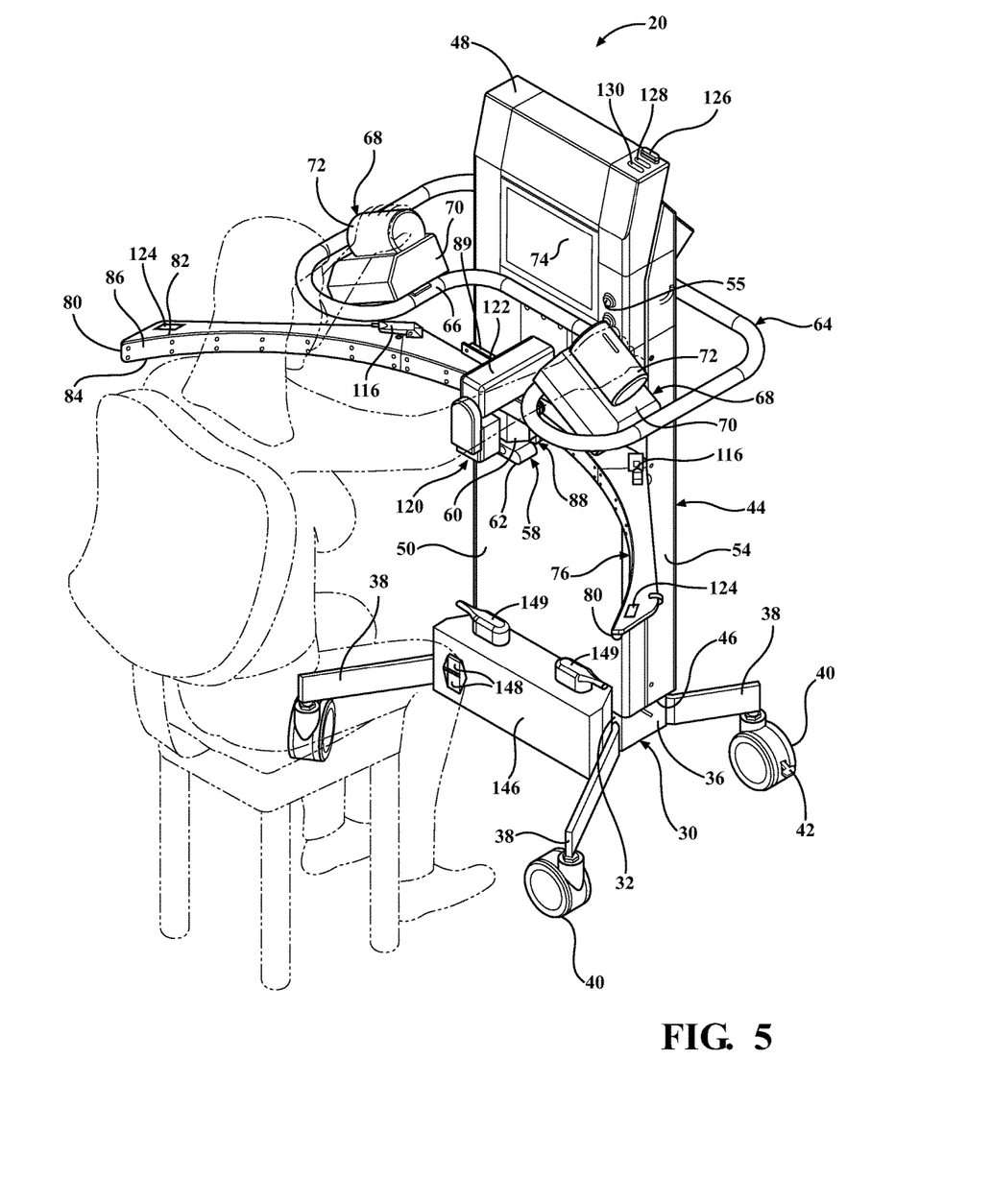
FIG. 5 is a perspective front view of the preferred arrangement of the diagnostic apparatus illustrating the rail disposed in surrounding relationship with the breasts of a patient positioned in a testing position.

Referring to the Figures, wherein like numerals indicate corresponding parts throughout the several views, a diagnostic apparatus 20 is generally shown for detecting a presence of breast cancer in a patient disposed in a testing position. As best shown in FIG. 5, in a preferred arrangement, the testing position is defined by the patient sitting in a standard doctor office chair. However, the testing position could also include a patient standing in an examination room, sitting in a wheel chair, sitting on an examination table, or other style of seating surface.

The diagnostic apparatus 20 includes a power source 22 of electrical energy for providing electrical energy to the diagnostic apparatus 20. The diagnostic apparatus 20 further includes a controller 24 having a processor 26 for executing diagnostic operations to control the diagnostic apparatus 20. The controller 24 also includes a hard drive 28 for storing test information such as thermographic and three-dimensional images, as will be described in greater detail below, that are received from the executed diagnostic operations.

In a preferred arrangement, the diagnostic apparatus 20 includes a base 30 that has a rectangular boundary border which includes a front wall 32, a back wall 34 and a pair of side walls 36 interconnecting the front wall 32 and the back wall 34 at four base corners. A plurality of legs 38 each extend outwardly from one of the base corners of the base 30 to a terminal end. A caster 40 is connected to the terminal end of each of the legs 38 for establishing rolling movement of the diagnostic apparatus 20 over a floor in an examination room. In the preferred arrangement, the casters 40 are relatively large in size to ease rolling movement of the diagnostic apparatus 20 to various positions within the examination room. Each caster 40 includes a lock 42 for selectively locking the casters 40 to prevent the rolling movement of the diagnostic apparatus 20 during testing to ensure the accurate operation of the diagnostic apparatus 20. Each lock 42 can include an actuator that is electrically connected with the controller 24 for automatically locking the caster 40 in response to a command sent from the controller 24.

A housing 44 is connected with the base 30 and has a generally cuboid shape that includes a bottom periphery 46, a top periphery 48, a front periphery 50, a rear periphery 52 and a pair of side peripheries 54. However, the housing 44 could have other shapes without departing from the scope of the subject disclosure. A power button 55 is disposed on the front periphery 50 of the housing 44 for turning the diagnostic apparatus 20 on and off. The power button 55 could be located at other locations of the housing 44 and could alternatively be in the form of a switch or other activation mechanism without departing from the scope of the subject disclosure. Further, a first graphical user interface 56 is disposed on the rear periphery 52 of the housing 44 and electrically connected to the controller 24 for presenting operational data related to the diagnostic apparatus 20 to a technician and for receiving input data from the technician when the diagnostic apparatus 20 is turned on. For example, the first graphical user interface 56 is configured to display a start/stop test option to allow the technician to start and stop a testing procedure of the diagnostic apparatus 20. Further, the first graphical user interface 56 is configured to display a help/information button that the technician may utilize if they have questions during operation of the diagnostic apparatus 20. In the preferred arrangement, the first graphical user interface 56 is a touch-screen interface to allow the technician to easily and quickly input information into the diagnostic apparatus 20. However, an input device like a keyboard may alternatively or additionally be connected thereto to provide input to the diagnostic apparatus 20 without departing from the scope of the subject disclosure.

A camera assembly 58 is supported by the housing 44 for recording images of the breasts of the patient in the testing position. The camera assembly 58 includes a three-dimensional camera 60 for recording three-dimensional images of the breasts of the patient and a thermographic camera 62 for recording thermographic images of the breasts of the patient. The three-dimensional camera 60 is capable of providing an accurate three-dimensional, color, model of the breasts of the patients that can be utilized to identify a nipple and breast profile for use in correlating subsequent analyses. The three-dimensional breast model captured by the three-dimensional camera includes the exact size and shape of the breasts and therefore can be used to measure and identify features indicative of cancer such as flat spots, bulges, depressions and the like in the breasts of the patient. In the preferred arrangement, the thermographic camera 62 has a fixed focal lens (rather than a variable lens) and is small and compact in size to reduce manufacturing and distribution costs for the diagnostic apparatus 20. However, other types of thermographic cameras 62 could be utilized without departing from the scope of the subject disclosure.

A handle 64 is connected to the front periphery 50 of the housing 44 and is spaced from and surrounds the rear and side peripheries 52, 54 of the housing 44. The handle 64 is U-shaped to define a pair of limbs 66 that extend outwardly from the front periphery 50 of the housing 44. A pair of cold bars 68 are supported by the limbs 66 within the handle 64 for receiving the hands of the patient and for protecting the cold bars 68 during transportation and rolling movement of the diagnostic apparatus 20 about the examination room.

Each of the cold bars 68 include a chassis 70 that has a generally box shape and a pommel 72 of an aluminum material that is connected with the chassis 70 for receiving a respective hand of the patient. The pommel 72 could be made out of other materials, e.g., other metals, without departing from the scope of the subject disclosure. The chassis 70 of each of the cold bars 68 engages one of the limbs 66 of the handle 64 to space the pommels 72 from the housing 44. The pommel 72 of each of the cold bars 68 is angled from the handle 64 toward the floor for providing an ergonomic grip space on the cold bars 68 for the patient.

An arc-shaped rail 76 extends perpendicularly from the front periphery 50 of the housing 44 in a horizontal plane P and terminates at a pair of rail ends 80 disposed in an extended position spaced and aligned with one another. As best shown in FIG. 5, the arc-shaped rail is ultimately disposed in spaced and surrounding relationship to the breasts of the patient in the testing position to align each rail end 80 with a side of a respective breast of a patient. Put another way, one rail end 80 is disposed in aligned relationship with a side of the left breast and the other rail end 80 is disposed in aligned relationship with a side of the right breast when the patient is disposed in the testing position. The rail 76 extends between a top margin 82 and a bottom margin 84 and presents a front surface 86 therebetween. The rail 76 could have other shapes, but the rail ends 80 should be spaced and aligned with the breasts of the patient when the patient is in the testing position.

Figure 4:
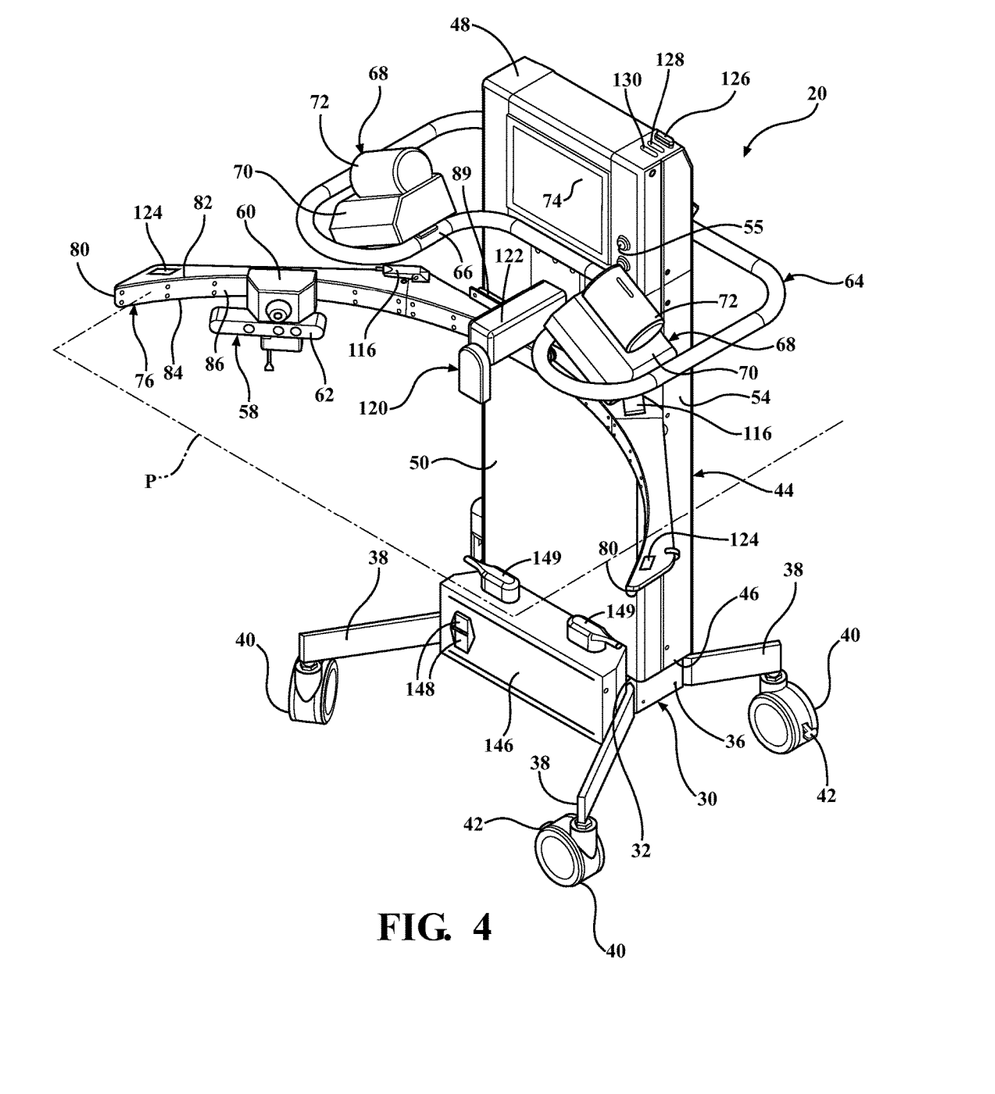
FIG. 4 is a perspective front view of the preferred embodiment of the diagnostic apparatus illustrating sliding movement of a camera assembly along a rail.

A trolley 88 interconnects the camera assembly 58 and the rail 76 and is slideable along the rail 76 for slideable movement between the rail ends 80 for allowing the camera assembly 58 to slide around the breasts of the patient and into alignment with the sides of the breasts. The sliding movement of the trolley 88 allows the camera assembly 58 to consecutively record images of the patient along different lengths of the rail 76. For example, FIG. 4 illustrates a position of the trolley 88 and camera assembly 58 being spaced toward the rail ends 80 relative to the position of the trolley 88 and camera assembly 58 shown in FIG. 1. The trolley 88, also facilitates recording images of the lymph nodes of the patient when the camera assembly 58 is disposed adjacent to the rail ends 80 and in alignment with the sides of the breasts of the patient. This is an improvement over traditional testing methods, like mammogram treatments, which are unable to utilize and take into account the lymph nodes during its analysis to detect for breast cancer. Furthermore, sliding movement of the trolley 88 in a single horizontal plane P reduces complexity and cost of the recording process as compared to the prior art imaging methods, and image to image accuracy is improved since the recorded images are lined up next to each other on the same horizontal plane P. Additionally, because the trolley 88 supports and moves both the three-dimensional camera 60 as well as the thermographic camera 62 together, a spatial relationship is maintained between the three-dimensional and thermographic cameras 62, and therefore data from each respective camera is easily and accurately compared and analyzed.

Figure 1:
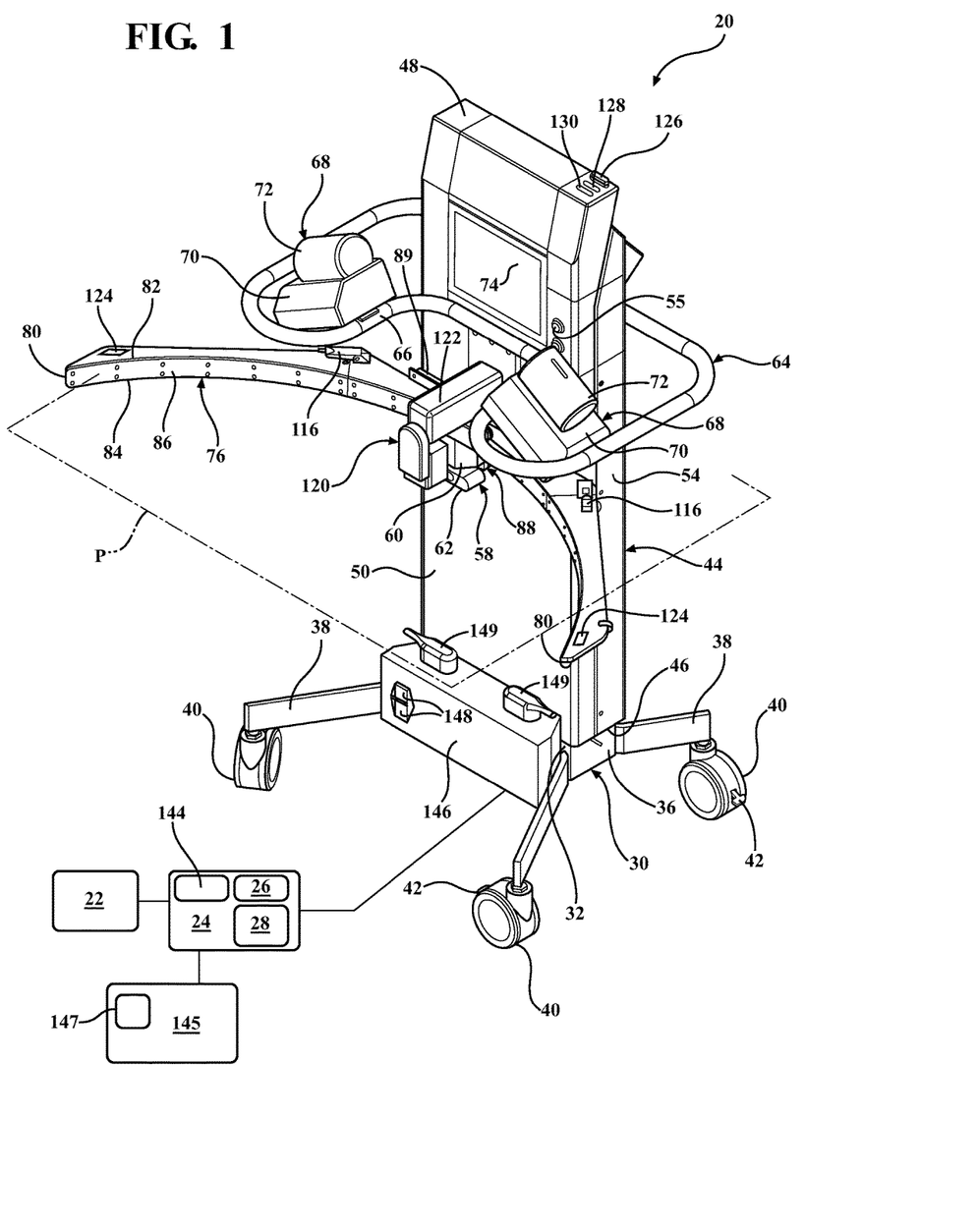
FIG. 1 is a perspective front view of the preferred arrangement of a diagnostic apparatus.

As best shown in FIG. 1, a cable guard 89 is positioned between the front periphery 50 of the housing 44 and the rail 76 for preventing various cables of the diagnostic apparatus 20 from interfering with movement of the trolley 88.

Figure 6:
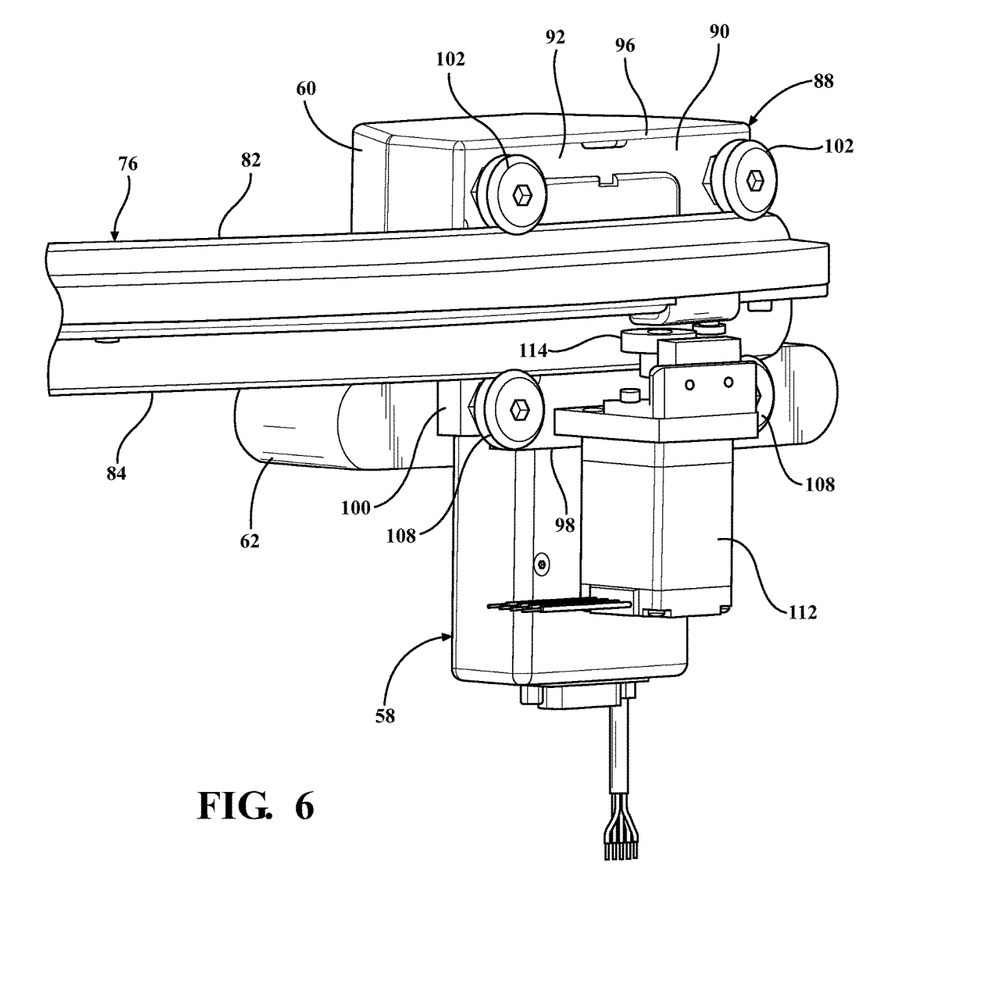
FIG. 6 is a perspective view of a trolley and camera assembly of the preferred arrangement of the diagnostic apparatus.
Figure 7:
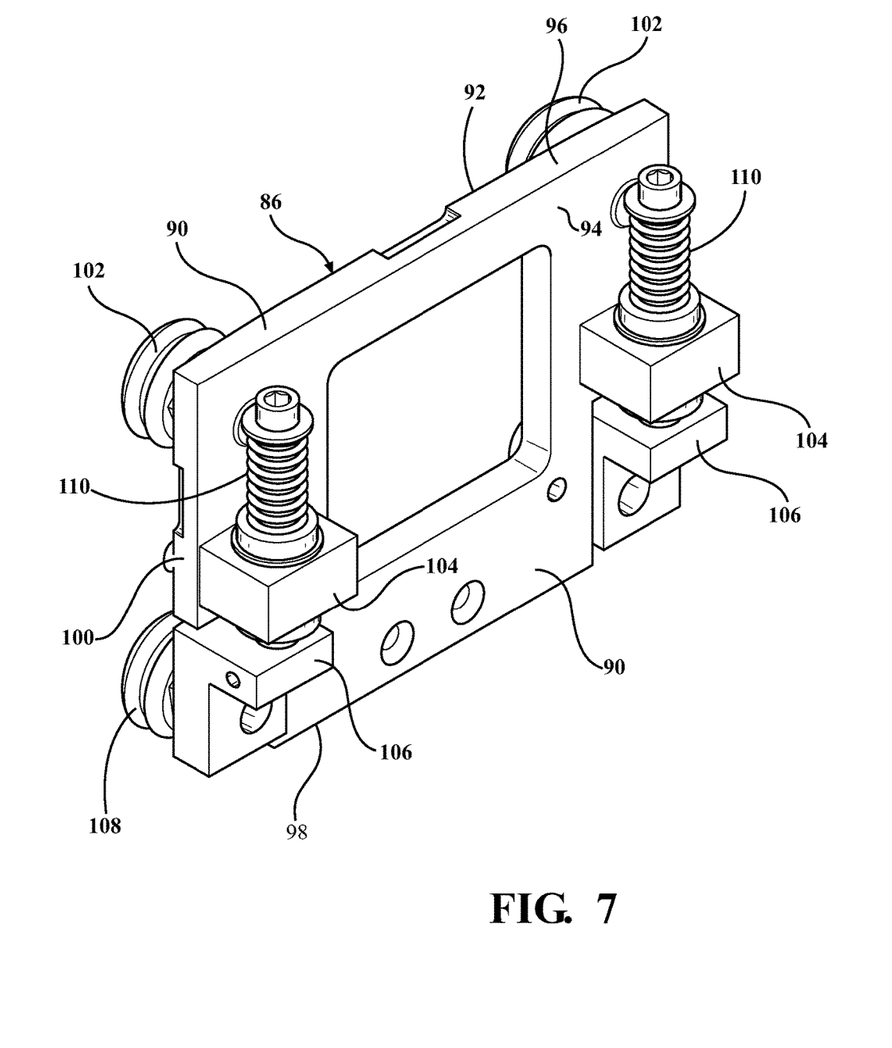
FIG. 7 is a perspective view of a backing of the trolley of FIG. 6.

As best shown in FIGS. 6-7, the trolley 88 includes a backing 90 that has a front face 92, a rear face 94, a top edge 96, a bottom edge 98, and a pair of side edges 100 that extend between the top and bottom edges 96, 98. A pair of upper wheels 102 are rotatably connected to and extend through the front face 92, each adjacent to the top edge 96 and one of the side edges 100, and a pair of upper blocks 104 each extend from the rear face 94 adjacent to one of the side edges 100. Furthermore, a pair of lower blocks 106 are each positioned below one of the upper blocks 104. A pair of lower wheels 108 each extend through one of the lower blocks 106 in spaced and parallel relationship with one of the upper wheels 102.

The upper wheels 102 are disposed against the top margin 82 of the rail 76 for rolling along the top margin 82 during movement of the camera assembly 58, and the lower wheels 108 are disposed against the bottom margin 84 of the rail 76 for rolling along the bottom margin 84 to provide for the sliding movement of the camera assembly 58 along the rail 76. A spring mechanism 110 connects the higher block 104 and the lower block 106 for biasing the upper and lower wheels 102, 108 against the rail 76 and for accommodating variances in the width of the rail 76. The trolley 88 further includes a trolley motor 112 that is connected to the rear face 94 of the backing 90. The trolley motor 112 has a driving wheel 114 that frictionally engages the rail 76 for providing the sliding movement of the camera assembly 58. In the preferred arrangement, the trolley motor 112 is a stepper motor, but other types of motors could be utilized. The trolley motor 112 is electrically connected to the controller 24 for controlling the movement of the trolley 88 along the rail 76. Furthermore, the front surface 86 in conjunction with the top and bottom margins 82, 84 of the rail 76 provide for a clean edge for the trolley 88 to roll on from position to position.

Figure 2:
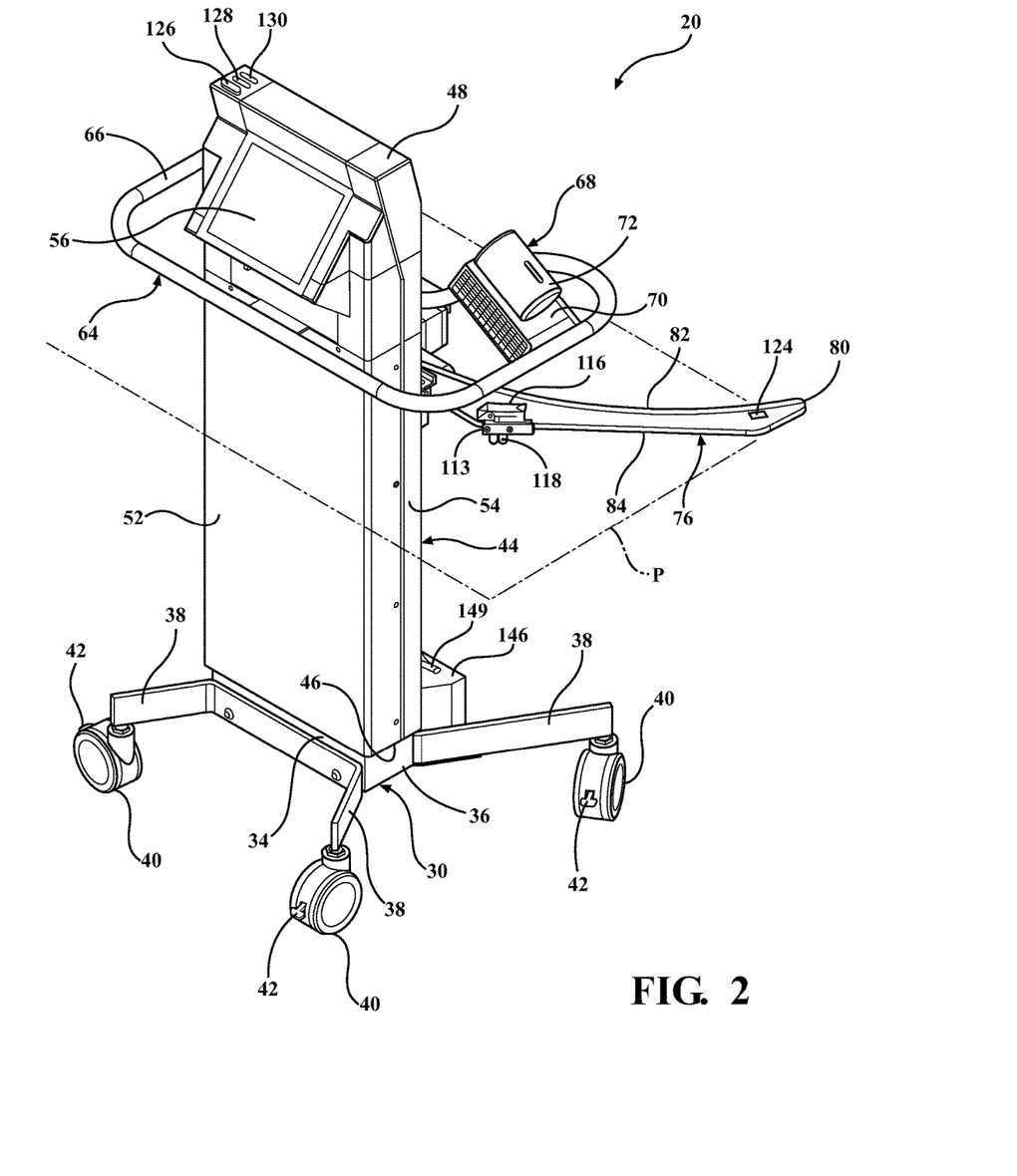
FIG. 2 is a perspective rear view of the preferred arrangement of the diagnostic apparatus.
Figure 3:
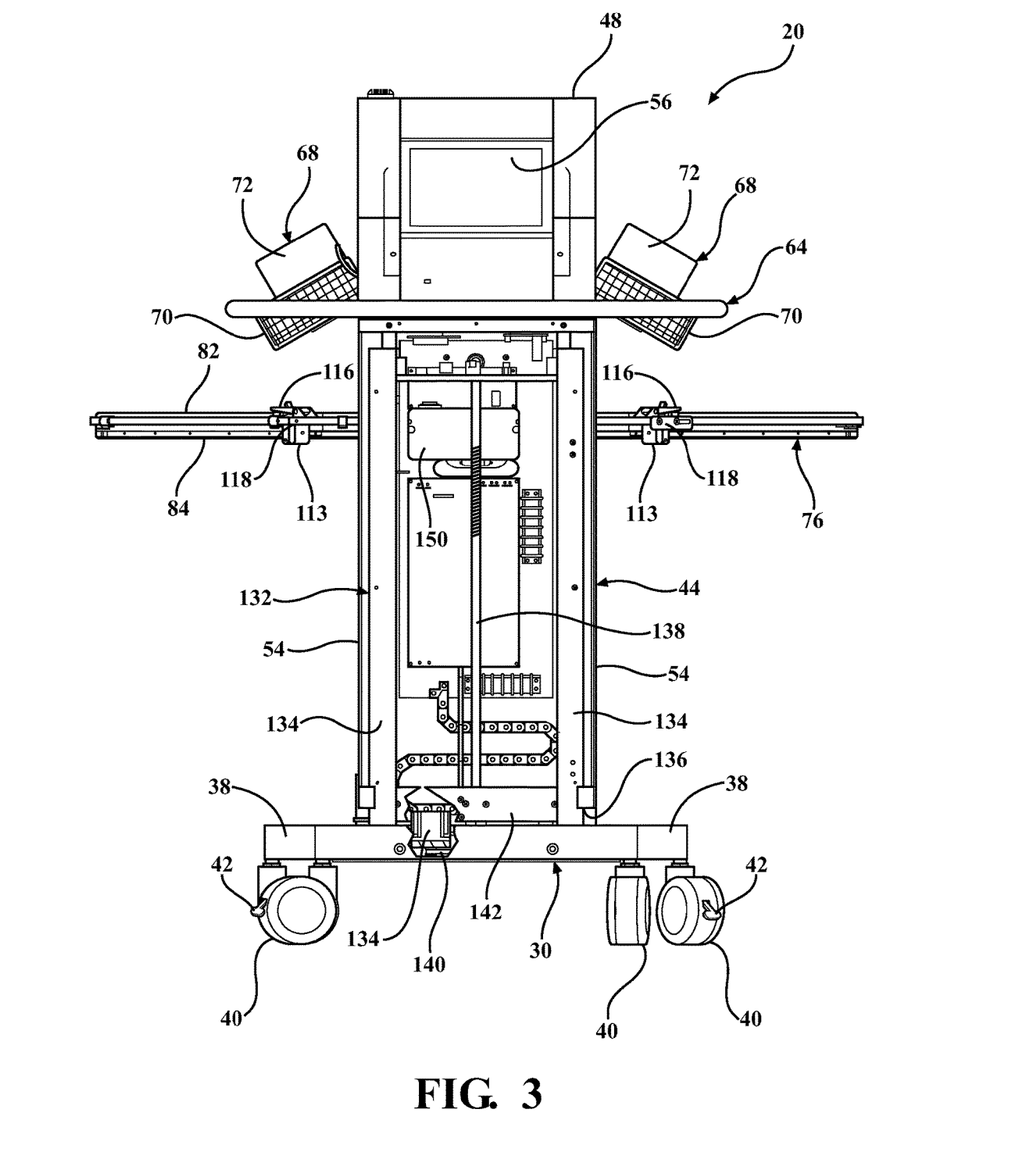
FIG. 3 is a cutaway back of the preferred arrangement of the diagnostic apparatus presenting tracks and a lead screw for vertically moving a housing.

As best shown in FIGS. 2 and 3, a pair of hinges 113 are disposed along the rail 76 in spaced relationship with one another for pivoting the rail ends 80 in the horizontal plane P from the extended position and toward the housing 44 to establish a compact position of the diagnostic apparatus 20. A pair of latches 116 are each pivotally disposed along the rail 76 adjacent to the hinges 113 for locking the rail 76 in the extended or the compact positions. A hinge sensor 118 is disposed adjacent to each of the hinges 113 to determine the position of the rail ends 80. The overall compact size of the diagnostic apparatus 20, established by the compact position, allows the diagnostic apparatus 20 to utilize minimal examination room space, eases shipment of the diagnostic apparatus 20 to different locations in vehicles and carriers, and allows the diagnostic apparatus 20 to be easily moved between examination rooms, even during the short period of time in which the patient waits for the doctor in the examination room.

The assembly further includes a black body radiator 120 preferably of a copper material for emitting heat toward the camera assembly 58. The black body radiator 120 provides a continuous surface maintained at a predetermined calibration temperature (32 degrees Celsius in the preferred arrangement) for use in calibrating the thermographic camera 62. The use of the black body radiator 120 to calibrate the camera assembly 58 prevents camera drift during the recording of the consecutive thermographic images, allowing the temperature in consecutive images to be accurately compared to each other. More specifically, when the thermographic camera 62 is aligned with the black body radiator 120, the thermographic camera 62 performs a non-uniformity correction (NUC) wherein all pixels may be set to the same value to provide a correction that removes camera drift. The NUC function normalizes all of the pixels (76,800 in the preferred arrangement) of the IR camera to exactly 32 degrees Celsius. The black body radiator 120 has a custom circuit to maintain the known temperature accurately. More specifically, the black body radiator 120 includes a thermocouple that is electrically connected with the controller 24 for monitoring and maintaining the temperature of the black body radiator 120. Other ranges of pixels and temperatures could be utilized. Further, the thermographic camera 62 may be calibrated between the recording of any number of images.

Moreover, the black body radiator 120 is coated with a matt-finish paint to minimize thermographic camera reflections to provide for a uniform temperature surface with high emissivity. This is contrary to a reflective surface of the black body radiator 120, which would cause the black body radiator 120 to pick up the reflection of the lens of the thermographic camera 62 and therefore increase the temperature of the thermographic readings within the thermographic images. Alternatively, other non-reflective materials like a flocking material, could be utilized to minimize thermographic camera reflections to provide the uniform temperature surface without departing from the scope of the subject disclosure.

A spacing member 122 interconnects the black body radiator 120 and the front periphery 50 of the housing 44 by a clearance distance for allowing the camera assembly 58 to slide along the rail 76 between the black body radiator 120 and the front periphery 50 of the housing 44. In the preferred arrangement, the black body radiator 120 is spaced one inch from the thermographic camera 62 when the camera assembly 58 is disposed in alignment with the black body radiator 120 to ensure that the thermographic camera 62 is accurately calibrated. Other distances could be utilized as is necessary to calibrate the thermographic camera. Additionally, the black body radiator 120 is pivotally connected to the spacing member 122 for allowing the black body radiator 120 to pivot out of alignment with the camera assembly 58. The black body radiator 120 could alternatively be slideably connected to the spacing member 122 to allow the black body radiator 120 to slide vertically or horizontally out of alignment with the camera assembly 58 without departing from the scope of the subject disclosure.

In order to determine the position of the camera assembly 58 along the rail 76, a pair of position sensors 124 are each disposed adjacent to one of the ends 80 of the rail 76. Further, the controller 24 is configured to monitor the number of steps taken by the trolley motor 112 to determine the position of the camera assembly 58 along the rail 76 at any time during the diagnostic test. Alternatively, the trolley motor could include an encoder that is electrically connected to the controller 24 to measure the position of the trolley motor 112. It should be appreciated that knowing the location of the camera assembly 58 ensures that the camera assembly 58 is in the proper position during all phases of testing.

A second graphical user interface 74 is disposed on the front periphery 50 of the housing 44 for presenting operational data related to the diagnostic apparatus 20 to the patient and for receiving input data from the patient before and during operation of the diagnostic apparatus 20. More specifically, the second graphical user interface 74 is electrically connected to the controller 24, and is configured to inquire about and receive information from the patient before the diagnostic test and then subsequently guide the patient through the testing procedure. Like the first graphical user interface 56, in the preferred arrangement, the second graphical user interface 74 is a touch-screen interface. However, an input device like a keyboard may alternatively or additionally be connected thereto to allow the patient to input information to the diagnostic apparatus 20. A speaker may be connected to the diagnostic apparatus 20 adjacent to the second graphical interface to play audio to the patient that correlates with the information presented on the second graphical user interface 74.

As an alternative or supplement to inputting information via the second graphical user interface 74, patients may also upload information to the internet from their home or other remote location such as a doctor's office. The input information may include the patient's personal and family medical histories. Such medical histories may include but are not limited to, any past or current medicines or medical operations such as a mastectomy, lumpectomy, hysterectomy and endometrial ablation. Additionally, the input information may include any present changes or concerns of the patient such as pain, color, physical distortion, etc. of the breast. Such input information may be considered in current or subsequent analyses to determine the likelihood of a presence of cancer, and may significantly affect the analyses. For example, the diagnostic apparatus and method can take into account the patient's medical history because a ratio of the temperature between breasts of the patient may change by approximately 20-30% based on the types of medications that the patient is taking or medical operations that the patient has undergone.

The second graphical user interface 74 and/or speakers are configured to alert the patient when each step of the testing procedure is about to begin. Furthermore, the second graphical user interface 74 and/or speakers instruct the patient on how to position themselves in the appropriate posture for each stage of the testing procedure. More specifically, the second graphical user interface 74 is electrically connected to the three-dimensional camera 60 to display a live three-dimensional image of the patient, along with live instructions to the patient to correct their posture, e.g., to move slightly forward or backward, left or right, to sit up, etc. In the event the patient does not correct their posture in a timely manner, an audible alarm may be produced by the speaker or the testing procedure may be stopped in its entirety. Further, the second graphical user interface 74 displays videos to the patient before the testing procedure which explain the benefits of using the diagnostic apparatus 20. Other videos could be displayed at different stages of the testing procedure.

Like the first graphical user interface 56, the second graphical user interface 74 is configured to display a start/stop test option to allow the patient to start and stop the testing procedure. Further, the second graphical user interface 74 is configured to display a help/information button that the patient may utilize if they have questions about operating the diagnostic apparatus 20. Additionally, the second graphical user interface 74 includes a privacy button that the patient may push to notify technicians to remain out of the examination room so that the patient may disrobe and proceed with the testing procedure in privacy.

The first and second graphical user interfaces 56, 74 may present further forms of operational information to the patient/technician, such as whether the camera assembly 58 is in condition for operation, whether the power source 22 is properly connected, a list of tests to be performed, room characteristics, the status of the diagnostic apparatus 20, issues with the diagnostic apparatus 20 and explanations, test completion time, whether the privacy mode is activated, battery status, and other information. Furthermore, the controller 24 is configured to notify the patient via the second graphical user interface 74 and/or speakers that the testing procedure has been completed or aborted. Likewise, the controller 24 is configured to inform the technician via email, text message or the like that the testing procedure has been completed or aborted. This is particularly useful when the privacy mode is activated by the patient.

It should be appreciated that after the diagnostic apparatus 20 is placed in front of the patient by the technician and the patient is disposed in the testing position, testing can be initiated without further assistance from the technician since the diagnostic apparatus 20 is configured to allow the second graphical user interface 74 to easily transmit and receive information from the patient and guide the patient through the testing procedure. This advantageously provides for increased patient privacy and reduced operational costs since a technician does not need to be actively employed to assist the patient through the testing procedure. This leads to increased comfort for the patient as well as decreased costs to operate and perform the diagnostic test.

A plurality of sensors 126, 128, 130 are disposed on the housing 44 for recording various conditions within the examination room. For example an air flow sensor 126 is disposed on the housing 44 for measuring ambient air flow in the examination room, a temperature sensor 128 is disposed on the housing 44 for measuring the ambient temperature in the examination room, and a humidity sensor 130 is disposed on the housing 44 for measuring ambient humidity in the examination room. The controller 24 is electrically connected with the air flow, temperature and humidity sensors 126, 128, 130 and is configured to analyze the air flow, temperature and humidity of the examination room prior to and during examination of the patient to prevent inaccurate temperature readings by the thermographic camera 62.

With further reference to the air flow sensor 126, in the event that the air flow sensor 126 detects too much air movement in the examination room, the controller 24 instructs the technician, via the first graphical user interface 56 and/or speakers, to add baffles to the ceiling or other location around the diagnostic apparatus 20 and block unwanted air flow to prevent inaccurate recordings from the thermographic camera 62. Furthermore, if the air flow is too high, the controller 24 is configured to either entirely stop the examination procedure or allow the examination procedure to continue with a note on a subsequently provided diagnostic report that the air flow was too high.

In the preferred arrangement, the ideal temperature range in the examination room to operate the thermographic camera 62 is approximately 75 degrees Fahrenheit or less. This temperature range ensures that there is a sufficient temperature difference between the temperature of the examination room and the body temperature of the patient. In the event the temperature sensor 128 detects that the temperature in the examination room is above the upper threshold of this temperature range, the controller 24 instructs the technician, via the first graphical user interface 56 and/or speakers, to lower the temperature in the examination room. If the temperature is too high, the controller 24 is configured to either stop the examination procedure or allow the examination procedure to continue with a note on a subsequently provided diagnostic report that the temperature was too high.

Regarding the humidity sensor 130, if the humidity sensor 130 detects that the humidity in the examination room is too high, the controller 24 instructs the technician via the first graphical user interface 56 and/or speakers to take appropriate action to reduce the humidity in the examination room. If the humidity is too high, the controller 24 may either stop the examination procedure or allow the examination procedure to continue with a note on a subsequently provided diagnostic report that the humidity was too high.

As best shown in FIG. 3, the diagnostic apparatus 20 also includes a lifting mechanism 132 for vertically moving the housing 44 relative to the base 30 to adjust the height of the cold bars 68 and the camera assembly 58 for providing an ergonomic grip of the cold bars 68 by various patients and for placing the camera assembly 58 in vertical alignment with the breasts of the patient. Although the patient sits in a standard doctor's office chair in the preferred arrangement (as best shown in FIG. 5), the lifting mechanism 132 allows the diagnostic apparatus 20 to accommodate differently sized patients (height and weight) as well as those patients who must stand or sit in a wheel chair or other style of a seating surface. Additionally, in event that the entire vertical shape of the breasts of the patient are not completely captured by the camera assembly 58 in the initial horizontal position, the lifting mechanism 132 can move the housing 44 up and down to take multiple images that are vertically stacked on top of one another to capture the entirety of the breasts in both the horizontal and vertical directions.

The lifting mechanism 132 includes a pair of tracks 134 that extend upwardly from the base 30 in spaced and parallel relationship with one another and connected to the housing 44. A channel 136 is defined by the bottom periphery 46 of the housing 44 and telescopically receives the tracks 134 for allowing the housing 44 to vertically and linearly move along the tracks 134. A lead screw 138 extends upwardly from the base 30 between the tracks 134, and a driving motor 139 engages the base 30 and includes a piston that is rotatably connected with the lead screw 138 for providing rotary motion of the lead screw 138. A belt 140 is disposed about the piston of the driving motor 139 and the lead screw 138 for transferring rotating motion of the piston to the lead screw 138. Further, a cross-member 142 that has a cuboid shape extends transversely between the side peripheries 54 at the bottom periphery 46 of the housing 44. The lead screw 138 threadedly extends through the cross-member 142 for converting rotary motion of the lead screw 138 into vertical and linear motion of the cross-member 142 along the lead screw 138 to provide for the vertical and linear movement of the housing 44. The lifting mechanism 132 further includes a pair of supporting rods which are surrounded by the tracks 134 and extend from the base 30 and through the cross-member 142 in spaced and parallel relationship with the lead screw 138 for guiding the cross-member 142 during vertical movement of the housing 44.

The controller 24 is electrically connected to the driving motor 139 for controlling the driving motor 139 to control the vertical movement of the housing 44. Furthermore, like the trolley motor 112, the driving motor 139 is a stepper motor, and is electrically connected to the controller 24 to monitor the number of steps taken by the trolley motor 112 to determine the vertical position of the housing 44 and components of the lifting mechanism 132 at any time during the diagnostic test. Alternatively, the driving motor 139 could have an encoder that measures the position of the driving motor 139, housing 44 and components of the lifting mechanism 132 without departing from the scope of the subject disclosure.

The controller 24 also includes a wireless communication module 144, such as a Wi-Fi card, for connecting with a cloud server 145 for transmitting information to and from the cloud server 145. The controller 24 is further electrically connected with the camera assembly 58 for receiving the three-dimensional and thermographic images from the camera assembly 58 and transmitting them to the cloud server 145 for subsequent processing at the cloud server 145. The connection between the controller 24 and the cloud server 145 allows processing of data captured by the diagnostic apparatus 20 to be performed securely over the cloud server 145. Furthermore, the cloud server 145 ensures that data is not lost due to issues with the diagnostic apparatus 20 like a fire, flood or the like. Additionally, connecting to the cloud server 145 allows patient data to be transmitted between diagnostic apparatuses 20 in various locations, allowing patients to have tests performed analyzed, and reviewed by doctors and technicians at several different locations and times.

The cloud server 145 also provides for a reliable means for updating the software associated with the diagnostic apparatus 20 and allows input data from biopsies or other medical procedures to be downloaded to the controller 24 to adjust the testing procedure and analysis as appropriate. Moreover, the cloud server 145 monitors the operation of the diagnostic apparatus 20 to ensure that it is performing correctly. For example, if the camera assembly 58 moves along the rail 76 at a faster speed in a second of two tests, the cloud server 145 may send a signal to the controller 24 to alert the technician via the first graphical user interface 56, speakers, text message, email or the like of the potential issue so that appropriate repairs may be made if necessary.

The cloud server 145 includes a database 147 for storing records of all tests performed with different diagnostic assemblies on different patients and at different locations. Over time, the cloud server 145 can evaluate hundreds of thousands of tested patients. This allows algorithms of the controller 24 to be improved to provide for improved sensitivity and specificity. Furthermore, the cloud server 145 can monitor a variety of other factors such as the effect of certain medicines, treatments or environmental factors. For example, by knowing the location of the patient, the cloud server 145 can measure the occurrences of breast cancer for those who live next to salt water, or it could measure the risk of obese women to develop breast cancer.

A power container 146 that has a rectangular shape is connected to the front periphery 50 of the housing 44. A pair of hooks 147 extend from the power container 146 in spaced and parallel relationship for receiving a wrapped power cable. The power source 22 includes a pair of power sockets 148 that are defined by the power container 146 for electrically connecting the diagnostic apparatus 20 with a wall socket or other AC/DC power connection. The power source 22 further includes a backup battery 150 that engages the housing 44 for providing backup power to the diagnostic apparatus 20 in the event of a power failure. The backup battery 150 is adapted to allow the thermographic camera 62 to be powered for up to four hours. This is greater than the minimum warmup time of the thermographic camera 62 of approximately 30 minutes. The power source 22 and controller 24 are configured to automatically warmup the thermographic camera 62 at least minutes prior to upcoming tests.

Figure 8:
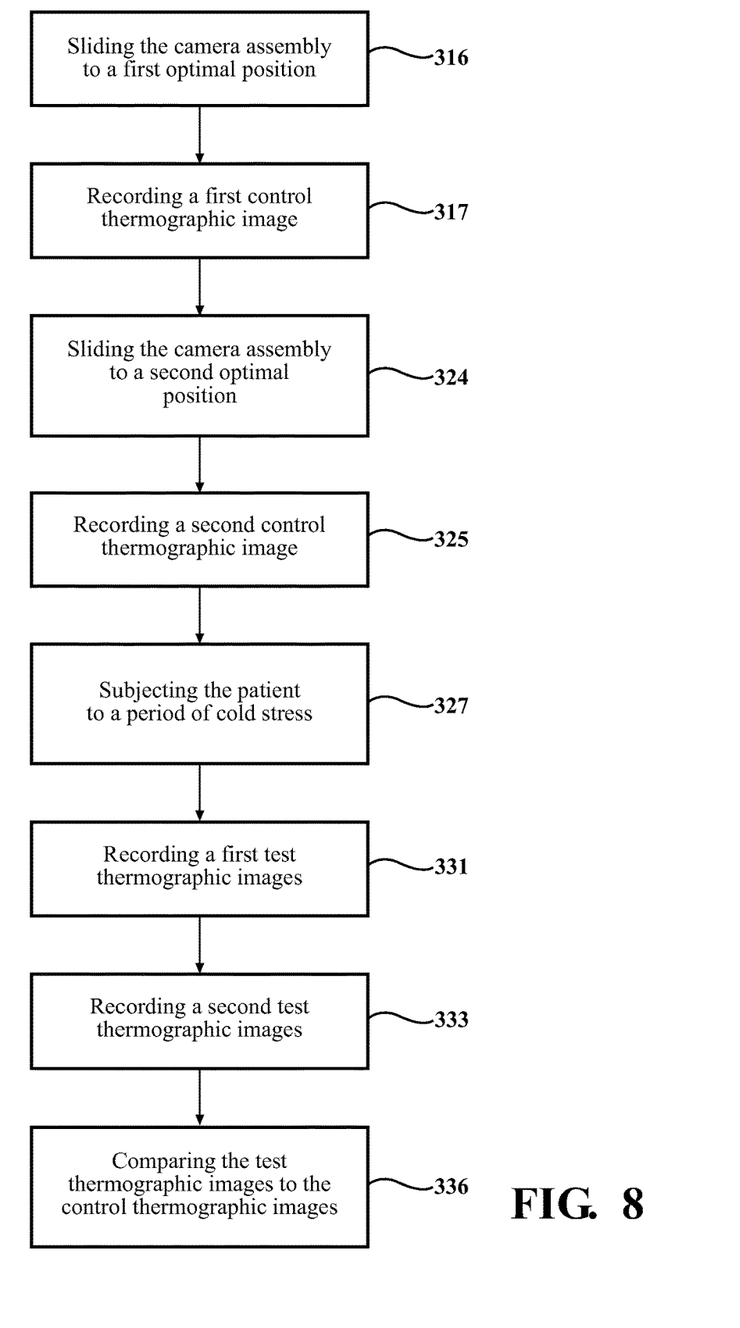
FIG. 8 is a flow diagram of a first embodiment of a method of examining breasts of a patient in an examination room to detect for potential breast cancer.
Figure 9:
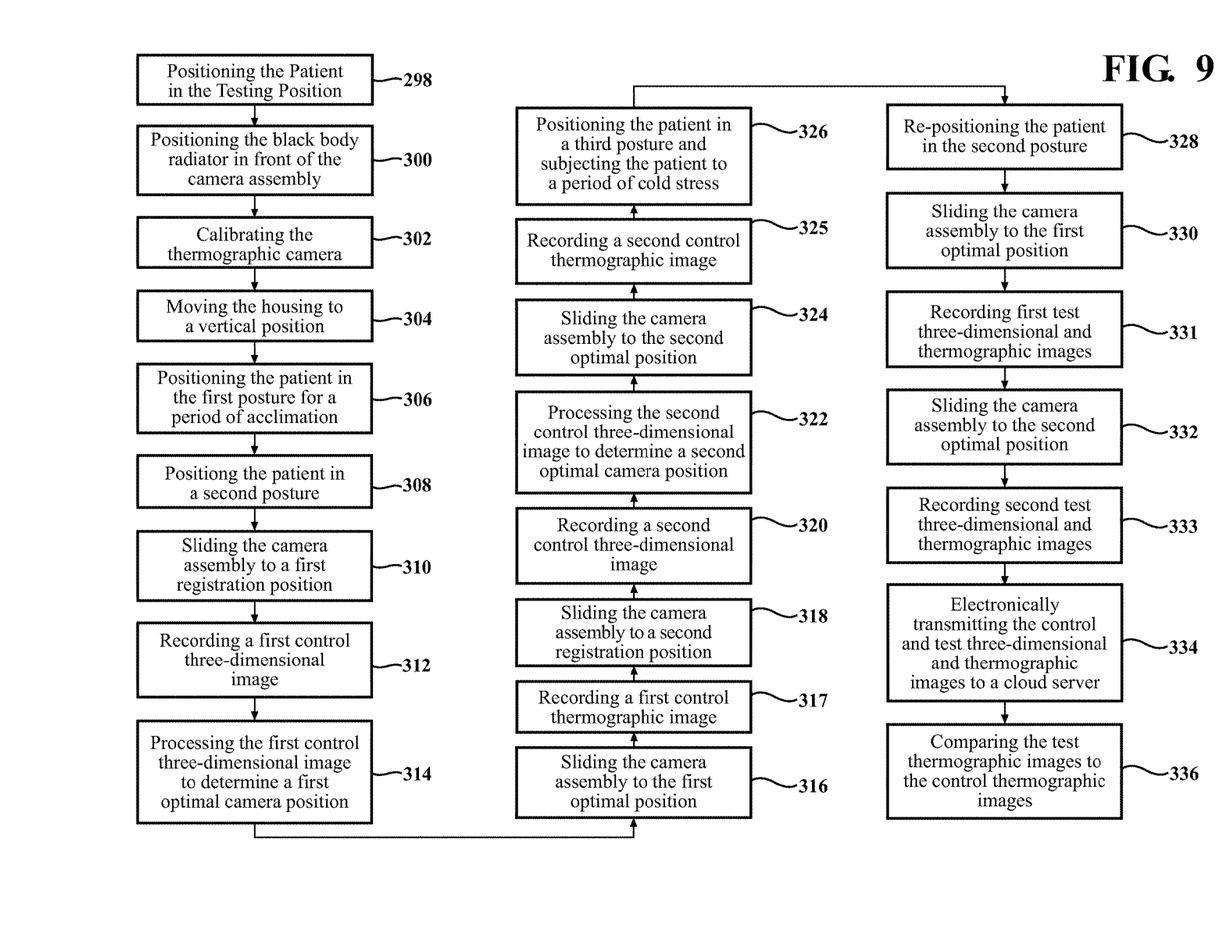
FIG. 9 is a flow diagram of a second embodiment of a method of examining breasts of a patient in an examination room to detect for potential breast cancer.

With reference to FIGS. 8 and 9, a method of examining breasts of a patient in an examination room to detect for potential breast cancer using a diagnostic apparatus 20 is also disclosed. The method begins by 298 positioning the patient in the testing position. As previously mentioned, the patient may be standing, sitting in a doctor office chair, sitting in a wheel chair, or the like in the testing position. The examination by the diagnostic apparatus proceeds by having a technician move the diagnostic apparatus 20 in front of the patient and commencing operation of the diagnostic apparatus 20 to begin an examination of the breasts of the patient. The method proceeds by 300 positioning a black body radiator 120 in alignment with the camera assembly 58. More specifically, the camera assembly 58 is slid along the rail 76 to define a calibration position in alignment with the black body radiator 120. Once the camera assembly 58 is in the calibration position, the method proceeds by 302 emitting heat from the black body radiator 120 and calibrating the thermographic camera 62 based on the heat emitted from the black body radiator 120.

The method proceeds by 304 moving the housing 44 to a vertical position wherein the camera assembly 58 is vertically aligned with the breasts of the patient and the cold bars 68 are ergonomically positioned to accommodate for the height and arm length of the patient. This ergonomic position provides for increased comfort of the patient and maintains the arms of the patient in a position spaced from the breasts of the patient.

Once the housing 44 is moved to an ergonomic position, the method proceeds by 306 positioning the patient in a first posture for a predetermined period of acclamation to acclimate the breasts of the patient to the ambient temperature within the examination room. In the preferred arrangement, the predetermined period of acclamation is approximately five minutes, however, the period of acclamation may be longer or shorter depending on the body type of the patient and the ambient conditions within the examination room. The first posture preferably includes positioning the hands of the patient on their hips to space the arms from the breasts of the patient. However, other postures which keep the arms in spaced relationship to the breasts could also be used without departing from the scope of the subject disclosure.

During the period of acclamation, the thermographic camera 62 actively monitors the temperature of the breasts of the patient to determine when they reach steady state, thus indicating when it is appropriate to begin the next steps in the process. This minimizes the length of time necessary to complete the test since the patient may reach steady state before the full predetermined period of acclamation is completed.

Once the predetermined period of acclamation passes, the method proceeds by 308 positioning the hands of the patient behind their head of the patient to define a second posture. After the patient is positioned in the second posture, the method continues by 310 sliding the camera assembly 58 along the rail 76 to a first registration position that is spaced from the calibration position toward one of the rail ends 80 and aligned with a first side of the breasts of the patient. Once the camera assembly 58 is positioned in the first registration position, the method continues by 312 recording a first control three-dimensional image of the breasts of the patient. The method then proceeds by 314 processing the first control three-dimensional image with the controller 24 to determine a first optimal camera position for recording the lymph nodes on the first side of the breasts of the patient. For example, depending on a size of the patient's breasts, the first optimal position may be outward from the first registration position. In any event, the cosine rule is utilized by the controller 24 to determine the optimal camera position to ensure accurate temperature data is recorded of the sides of the breasts of the patient. Therefore, angles that would degrade the recorded thermographic images of the breasts are not utilized by the camera assembly 58. In more detail, to determine the first optimal position, the first control three-dimensional image is processed by the controller 24 via a breast extraction algorithm. The breast extraction algorithm draws a normal vector on the breast on the first side of the breasts that does not violate the cosine rule. Based on the normal vector, a path for the trolley 88 to the first optimal camera position is calculated using a coordinate system in terms of angles and degrees. It should be appreciated that these processing steps can be utilized to determine all additional optimal camera positions described below.

Once the first optimal camera position is determined, the method continues by 316 sliding the camera assembly 58 to the first optimal position and subsequently 317 recording a first control thermographic image with the camera assembly 58 disposed in the first optimal position. This step allows the camera assembly 58 to record and capture the lymph nodes on the first side of the breasts in the first control thermographic image.

After the first control three-dimensional and thermographic images are recorded, the method proceeds by 318 sliding the camera assembly 58 along the rail 76 to a second registration position being spaced from both the first registration and optimal positions and toward the other of the rail ends 80 in alignment with a second side of the breasts of the patient. The method then proceeds by 320 recording a second control three-dimensional image of the breasts of the patient, and then 322 processing the second control three-dimensional image with the controller 24 to determine a second optimal camera position for recording and capturing the lymph nodes on the second side of the breasts of the patient. It should be appreciated that additional optimal camera positions may be determined in accordance with the above described teachings. Such additional optimal camera positions may be located at the left front portion of the breasts, the right front portion of the breasts and the subclavian region of the breasts.

Once the second optimal camera position is determined, the method proceeds by 324 sliding the camera assembly 58 to the second optimal position and subsequently 325 recording a second control thermographic image with the camera assembly 58 disposed in the second optimal position. This step allows the camera assembly 58 to record and capture the lymph nodes on the second side of the breasts in the second control thermographic image.

The method proceeds by 326 positioning each of the hands of the patient on a cold surface to define a third posture, then 327 maintaining the third posture for a predetermined period of cold stress for cooling the hands of the patient. In the preferred arrangement, the predetermined period of cold stress is one minute, however, other periods of cold stress could be used without departing from the scope of the subject disclosure. The step of positioning each of the hands of the patient on a cold surface includes positioning each of the hands of the patient on the pommel 72 of one of the cold bars 68. It should be appreciated that the patient could be positioned in other postures to subject them to a period of cold stress. For example, a cold draft of air could be applied to the breasts, or other area of the patient, to provide for the period of cold stress.

After the period of cold-stress, the method proceeds by 328 re-positioning the patient in the second posture. Once the patient is in the second posture, the method proceeds by 330 sliding the camera assembly 58 along the rail 76 to the first optimal position and 331 recording at least one first test three-dimensional image and one first test thermographic image with the camera assembly 58 disposed in the first optimal position. Once again, this allows the camera assembly 58 to record and capture the lymph nodes on the first side of the breasts in the first test three-dimensional image and first test thermographic image. The method then continues with 332 sliding the camera assembly 58 along the rail 76 to the second optimal position and 333 recording a second test three-dimensional image and second test thermographic image with the camera assembly 58 disposed in the second optimal position. Again, this allows the camera assembly 58 to record and capture the lymph nodes on the second side of the breasts in the second test three-dimensional image.

After the test three-dimensional and thermographic images are recorded, the method proceeds by 334 electronically transmitting the control three-dimensional and thermographic images, and the test three-dimensional and thermographic images to the cloud server. The method then proceeds by 336 comparing the test thermographic images to the control thermographic images to identify regions of the breasts in which the temperature remained substantially unchanged by the predetermined period of cold stress. In the preferred arrangement, the step of comparing the test thermographic image to the control thermographic image is executed by the cloud server. However, the comparison could alternatively be conducted by the controller 24 at the diagnostic apparatus 20. The results of the comparison are transmitted back to the testing apparatus such that they may be reviewed by doctors and/or technicians. The results may be provided in the form of an electronic or written report to the doctor and/or patient and can even be provided to the patient via email, text message or the like.

As elaborated upon above, in the preferred arrangement of the method, thermographic images are recorded at two locations along the rail 76, namely the first and second optimal positions. However, additional images could also be recorded from additional locations along the rail 76. Further, it should be appreciated that because of the relative position of the camera assembly 58 to the breasts, images including substantially the whole breasts can be recorded, which can advantageously eliminate the need for splicing the thermographic images. Furthermore, in the preferred arrangement each thermographic image is approximately 11×8.5 inches to provide for a complete view of the breasts and to provide for relatively high pixel density, which allows for better analysis of the temperature of thermographic images.

The controller 24 is further configured to optimize the ratio of sensitivity and specificity of the testing procedure. These criteria may be changed based on preferences of the technician and patient, for example, to decrease the number of false positives detected. Furthermore, the controller 24 is configured to monitor the movement of the patient during the testing procedure via the three-dimensional camera 60 to ensure that the patient is positioned in the correct posture. If the controller 24 determines that the patient is positioned in the incorrect posture, it informs the patient, via the second graphical user interface 74 and/or speakers connected thereto of the need to correct their posture. For example, if the patient removes her hands from her hips during the acclimation period, the patient is informed via the second graphical user interface 74 of the need to correct her posture. If the posture is not corrected, the method may even be stopped by the controller 24.

The first control three-dimensional image (and subsequent three-dimensional images) can also utilized to allow the diagnostic apparatus 20 to be wheeled toward or away from the patient to align the camera assembly 58 by approximately 19 inches away from the breast midpoint of the patient. This ensures that subsequent thermographic images are focused and recorded with high temperature accuracy. In the preferred arrangement, the controller 24 is configured to only allow the camera assembly 58 to record images when the camera assembly 58 is spaced by approximately 19 inches from the breast midpoint, however, other distances could be utilized for different configurations of the camera assembly 58. The breast midpoint is defined by a point disposed halfway between a nipple and chest wall of the patient. Further, the cold bars 68 are positioned such that the patient may easily reach them while maintaining the approximately 19 inch distance from the camera assembly 58 to the breasts of the patient. The camera assembly 58 may alternatively be configured to slide the camera assembly 58 toward and away from the patient to ensure that the cameras 60, 62 are adequately focused. The controller 24 is configured to detect this distance and notify the technician or patient of the need to adjust the diagnostic apparatus 20. In the event this distance is not corrected, the method could be stopped by the controller 24.

The controller 24 is programmed to filter the background in each thermographic image to be consistent with one another to prevent inaccuracies in the thermographic images. In addition to software filters, a backdrop may be positioned behind the testing position to standardize the image behind the patient. The backdrop may be a hard or soft surface, and may further be made of a reflective material like a crinkled aluminum to reflect the temperature of the patient to minimize background temperature to improve temperature integrity. Additionally, the backdrop may utilize heated plates positioned on each side of the patient to accomplish this same result.

Furthermore, prior to starting the examination process, preliminary notices related to the examination process may be provided to the patient via email, text message or the like. Such notices may include a calendar reminder of a testing appointment or a reminder not to wear deodorant, drink caffeine or exercise during the day of testing.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims.

What is claimed is:

1. A diagnostic apparatus for detecting a presence of breast cancer in a patient disposed in a testing position, comprising;
    a housing including a front periphery and a rear periphery and a pair of side peripheries,
    a camera assembly supported by said housing for recording images of the breasts of the patient,
    a rail extending from said housing,
    a trolley supporting said camera assembly and slideably disposed along said rail for moving of said camera assembly along said rail to consecutively record images of breasts of the patient at different positions along said rail,
    a handle spaced from and surrounding said rear and side peripheries of said housing and connected to said front periphery of said housing,
    said handle being U-shaped to define a pair of limbs extending outwardly from said front periphery of said housing, and
    a pair of cold bars supported by said limbs within said handle for receiving the hands of the patient and for protecting said cold bars during rolling movement of said diagnostic apparatus.

2. The diagnostic apparatus as set forth in claim 1 wherein said rail extends along a horizontal plane for providing for said sliding movement of said trolley along said horizontal plane to allow said camera assembly to record images from said horizontal plane.

3. The diagnostic apparatus as set forth in claim 2 wherein said rail extends between a pair of rail ends disposed in spaced and aligned relationship with one another and each disposed in aligned relationship with a side of a respective breast of the patient to allow said camera assembly to record images of the lymph nodes of the patient when said camera assembly is disposed adjacent to said rail ends and in alignment with the sides of the breasts of the patient.

4. The diagnostic apparatus as set forth in claim 3 wherein said rail extends from said housing in an arc shape to dispose said rail in spaced and surrounding relationship with the breasts of the patient in the testing position.

5. The diagnostic apparatus as set forth in claim 3 further including at least one position sensor disposed on said rail adjacent to one of said rail ends for determining the position of said camera assembly along said rail.

6. The diagnostic apparatus as set forth in claim 2 further including a pair of hinges disposed along said rail in spaced relationship with one another to pivot said rail in said horizontal plane toward said housing and establish a compact position of said diagnostic apparatus.

7. The diagnostic apparatus as set forth in claim 1 further including a base, and a lifting mechanism interconnecting said housing and said base to vertically move said housing relative to said base and adjust a height of said camera assembly to dispose said camera assembly in vertically aligned relationship with the breasts of the patient in the testing position.

8. The diagnostic apparatus as set forth in claim 7 wherein said lifting mechanism includes a pair of tracks extending upwardly from said base and connected to said housing, and said lifting mechanism further includes a channel defined by said housing and telescopingly receiving said tracks for allowing said housing to vertically and linearly move along said tracks.

9. The diagnostic apparatus as set forth in claim 8 wherein said lifting mechanism further includes a lead screw extending upwardly from said base between said tracks,
    said lifting mechanism further including a cross-member extending transversely inside said housing, and said lead screw threadedly extending through said cross-member for converting rotary motion of said lead screw into vertical and linear motion of said cross-member along said lead screw to provide for said vertical movement of said housing relative to said base.

10. The diagnostic apparatus as set forth in claim 9 wherein said lifting mechanism further includes a driving motor including a piston rotatably connected with said lead screw for providing said rotary motion of said lead screw,
    said lifting mechanism further includes a belt disposed about said piston of said driving motor and said lad screw for transferring rotating motion of said piston to said lead screw.

11. The diagnostic apparatus as set forth in claim 1 wherein said rail extends between a top margin and a bottom margin, and said trolley includes a pair of upper wheels disposed against said top margin of said rail for rolling along said top margin during said movement of said camera assembly and a pair of lower wheels disposed against said bottom margin for rolling along said bottom margin of said rail during movement of said camera assembly along said rail.

12. The diagnostic apparatus as set forth in claim 11 further including a spring mechanism biasing said lower wheels and said upper wheels against said rail.

13. The diagnostic apparatus as set forth in claim 12 wherein said trolley further includes a backing having a front face and a rear face and a top edge and a bottom edge and a pair of side edges,
    a pair of upper blocks each extending from said rear face of said backing adjacent to one of said side edges,
    a pair of lower blocks each positioned below one of said upper blocks, said upper wheels rotatably connected to and extending through said front face adjacent to said top edge and one of said side edges, said lower wheels each extending through one of said lower blocks in spaced and parallel relationship with one of said upper wheels, and said spring mechanism extending between said upper and lower blocks for biasing said higher and lower blocks and said upper and lower wheels toward one another.

14. The diagnostic apparatus as set forth in claim 13 wherein said trolley further includes a trolley motor connected to said rear face of said backing and including a driving wheel frictionally engaging said rail for providing said sliding movement of said camera assembly.

15. The diagnostic apparatus as set forth in claim 1 wherein said camera assembly includes a thermographic camera, and a black body radiator is supported by said housing for emitting heat toward said camera assembly for calibrating said thermographic camera prior to recording images of the breasts of the patient.

16. The diagnostic apparatus as set forth in claim 15 wherein a spacing member interconnects said black body radiator and said housing by a clearance distance from said housing for allowing said camera assembly pass through said clearance distance between said black body radiator and said housing during sliding movement along said rail.

17. The diagnostic apparatus as set forth in claim 16 wherein said black body radiator is spaced by approximately one inch from said thermographic camera when said camera assembly is disposed in alignment with said black body radiator.

18. The diagnostic apparatus as set forth in claim 16 wherein said black body radiator is pivotally connected to said spacing member for allowing said black body radiator to pivot out of alignment with said camera assembly and to allow said camera assembly to record images of the patient.

19. The diagnostic apparatus as set forth in claim 1 wherein said camera assembly further includes a three-dimensional camera for recording three-dimensional images of the breasts of the patient.

* * * * *